United States Patent
Akingba et al.

(10) Patent No.: US 9,623,207 B2
(45) Date of Patent: Apr. 18, 2017

(54) DIRECTIONAL GUIDE CATHETER ASSEMBLY

(71) Applicants: A. George Akingba, Carmel, IN (US); Frank J. Fischer, Jr., Bloomington, IN (US)

(72) Inventors: A. George Akingba, Carmel, IN (US); Frank J. Fischer, Jr., Bloomington, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 134 days.

(21) Appl. No.: 14/209,291

(22) Filed: Mar. 13, 2014

(65) Prior Publication Data

US 2014/0276617 A1   Sep. 18, 2014

Related U.S. Application Data

(60) Provisional application No. 61/778,589, filed on Mar. 13, 2013.

(51) Int. Cl.
*A61M 5/00* (2006.01)
*A61M 25/01* (2006.01)
*A61M 25/00* (2006.01)

(52) U.S. Cl.
CPC ..... *A61M 25/01* (2013.01); *A61M 2025/0006* (2013.01); *A61M 2025/0008* (2013.01)

(58) Field of Classification Search
CPC .............. A61M 25/01; A61M 25/0105; A61M 25/0133; A61M 25/0136; A61M 25/0606; A61M 25/0625; A61M 2025/0006; A61M 2025/0008; A61M 25/0147; A61M 25/0144; A61B 17/3415
USPC ....... 604/95.04, 164.13, 171, 506, 510, 528, 604/95.01
See application file for complete search history.

(56) References Cited

U.S. PATENT DOCUMENTS

| | | | | |
|---|---|---|---|---|
| 5,366,441 A * | 11/1994 | Crawford | .......... | A61M 25/0606 604/159 |
| 5,545,200 A * | 8/1996 | West | .................. | A61B 18/1492 606/29 |
| 5,879,295 A * | 3/1999 | Li | ...................... | A61B 18/1492 600/373 |
| 6,071,279 A * | 6/2000 | Whayne | ............. | A61B 18/1492 606/41 |
| 2006/0135961 A1* | 6/2006 | Rosenman | ........ | A61M 25/0045 606/108 |

(Continued)

*Primary Examiner* — Justine Yu
*Assistant Examiner* — Tiffany Legette
(74) *Attorney, Agent, or Firm* — Quarles & Brady LLP (57) ABSTRACT

A guide catheter assembly includes an outer sheath and an inner catheter disposed, at least partially, within the outer sheath. A tether tethers the inner catheter to the outer sheath. The guide catheter assembly has a first configuration where the tether is untensioned and distal ends of the outer sheath and inner catheter are pointing in a first direction. In a second configuration of the guide catheter assembly, the tether is tensioned, the distal end of the outer sheath is pointing in the first direction, the distal end of the inner catheter is pointing in a second direction that is different from the first direction, and the tether is oriented at an angle different from both the first direction and the second direction.

18 Claims, 7 Drawing Sheets

(56) References Cited

U.S. PATENT DOCUMENTS

2012/0259206 A1* 10/2012 Roberts ............ A61M 16/0488
600/424

* cited by examiner

DIRECTIONAL GUIDE CATHETER ASSEMBLY

CROSS-REFERENCES TO RELATED APPLICATIONS

This application claims priority based on U.S. Provisional Patent Application No. 61/778,589 filed Mar. 13, 2013.

STATEMENT REGARDING FEDERALLY SPONSORED RESEARCH

Not Applicable.

BACKGROUND OF THE INVENTION

1. Field of the Invention

The present disclosure relates generally to the field of vascular intervention, and more particularly to a guide catheter assembly for facilitating direction changes in percutaneous endovascular procedures.

2. Description of the Related Art

Diagnosis and treatment of vascular conditions are commonly performed using percutaneous endovascular procedures, which involve the insertion of a catheter or the like into a blood vessel or artery of the vascular system. Known catheterization procedures include positioning and using stents and balloons within constricted vessels or arteries, and intravenous administering of bloods, drugs and other fluids. The first step in these procedures is establishing a site through the skin by which access is made to the blood vessel or artery. A wire guide then is introduced into the vessel or artery, and a guide catheter is used to assist in advancing the wire guide to a desired location. A working catheter may then be advanced to the desired location over the wire guide in a safe and atraumatic fashion.

Typically, pre-shaped wire guides and/or guide catheters are used to move the wire guide to the desired location within the vascular system. However, because of the convoluted nature of the pathways within the vascular system and the fact that locations may vary from one individual to another, the use of pre-shaped wire guides and/or guide catheters may require clinicians to stock multiple shapes and sizes of wire guides and/or guide catheters to account for potential variations. Further, use of these pre-shaped wire guides and/or guide catheters may require a time consuming trial and error process of inserting and removing different pre-shaped wire guides and/or guide catheters until the desired location is successfully reached. Yet further, the stiffness of the working catheter may cause a properly positioned wire guide, having a pre-shaped curve, to flip back into a straight configuration when the working catheter is inserted over the wire guide, thus making some sharp direction changes nearly impossible to achieve.

Additionally, it has proven to be difficult, if not impossible in some cases, to reverse the direction of the wire guide advancement through the initial access site. For example, after introducing a wire guide in the retrograde direction, it may be necessary or desirable to advance the wire guide into the vessel or other structure in the antegrade direction. A new access site in the opposite direction normally must be established to permit the advancement of the wire guide and, ultimately, working catheter in the opposite direction. Preparing a new access site is undesirable since it may require additional time and costs and may increase discomfort and the risk of infection to the individual. In addition, certain anomalies, such as obesity, may prohibit use of a desired access point in a desired direction for some individuals.

The present disclosure is directed toward one or more of the problems set forth above.

SUMMARY OF THE INVENTION

In one aspect, a guide catheter assembly includes an outer sheath and an inner catheter disposed, at least partially, within the outer sheath. A tether tethers the inner catheter to the outer sheath. The guide catheter assembly has a first configuration where the tether is untensioned and distal ends of the outer sheath and inner catheter are pointing in a first direction. In a second configuration of the guide catheter assembly, the tether is tensioned, the distal end of the outer sheath is pointing in the first direction, the distal end of the inner catheter is pointing in a second direction that is different from the first direction, and the tether is oriented at an angle different from both the first direction and the second direction.

In one version of the guide catheter assembly, the inner catheter is greater in length than the outer sheath. The second direction may be opposite the first direction. A first handle may be disposed along a proximal end of the inner catheter and a second handle may be disposed along a proximal end of the outer sheath, wherein the first handle is closer to the second handle in the second configuration than in the first configuration. A plurality of direction indicators may be positioned along a proximal end of the inner catheter, wherein one of the plurality of direction indicators corresponds to the second configuration. The guide catheter assembly may include a locking device for fixing a position of the inner catheter relative to the outer sheath at one of a continuum of positions between the first configuration and the second configuration.

In one version of the guide catheter assembly, the tether includes a flexible thread having: a first end connected to a proximal end of the inner catheter; a first segment disposed within the inner catheter; a second segment disposed within a space defined by an outer diameter of the inner catheter and an inner diameter of the outer sheath; and a second end connected to a proximal end of the outer sheath. The guide catheter assembly may include a first threaded fitting connected to the proximal end of the inner catheter and a second threaded fitting connected to the proximal end of the outer sheath, wherein the first end of the flexible thread is connected to the inner catheter by the first threaded fitting and the second end of the flexible thread is connected to the outer sheath by the second threaded fitting.

In another version of the guide catheter assembly, a first end of the tether is connected to the distal end of the inner catheter and a second end of the tether is connected to the distal end of the outer sheath. The tether may include a wall segment of one of the inner catheter and the outer sheath.

In another aspect, a method of positioning a guide catheter assembly includes moving the guide catheter assembly from a first configuration to a second configuration. This moving step includes pointing a distal end of an inner catheter and a distal end of an outer sheath in a first direction, sliding at least a segment of the inner catheter within the outer sheath, tensioning a tether, and pointing the distal end of the inner catheter in a second direction that is different from the first direction. The tensioning step may include limiting a range of movement of the distal end of the inner catheter relative to the distal end of the outer sheath using the tether. The method may further include locking the inner catheter relative to the outer sheath at one of a continuum of positions between the first configuration and the second configuration.

In still another aspect, a method of performing a percutaneous endovascular procedure on an individual using a guide catheter assembly includes inserting a wire guide into a vessel of the individual in a first direction, inserting the guide catheter assembly over the wire guide, and moving the guide catheter assembly from a first configuration to a second configuration. The moving step includes pointing a distal end of an inner catheter and a distal end of an outer sheath in the first direction, sliding at least a segment of the inner catheter within the outer sheath, tensioning the tether, and pointing the distal end of the inner catheter in a second direction. The method also includes moving a distal end of the wire guide through the distal end of the inner catheter in the second direction.

In the method of performing a percutaneous endovascular procedure, the tensioning step may include limiting a range of movement of the distal end of the inner catheter relative to the distal end of the outer sheath using the tether. The method may further include retracting the wire guide such that the distal end of the wire guide is received entirely within the guide catheter assembly prior to the first moving step. In the method, the sliding step may include moving a proximal end of the outer sheath to a direction indicator of a proximal end of the inner catheter. In the method, the first moving step may further include locking the inner catheter relative to the outer sheath to maintain the second configuration.

In the method of performing a percutaneous endovascular procedure, the first inserting step may include inserting the wire guide in a retrograde direction with respect to a blood flow direction and the step of moving the distal end of the wire guide may include moving the distal end of the wire guide in an antegrade direction with respect to the blood flow direction. The method may further include relaxing the guide catheter assembly, at least in part, by sliding at least a segment of the inner catheter out of the outer sheath and untensioning the tether; moving the guide catheter assembly further within the vessel in the second direction; moving the guide catheter assembly from a third configuration to a fourth configuration, at least in part, by: pointing the distal end of the inner catheter and the distal end of the outer sheath in the second direction; sliding at least the segment of the inner catheter within the outer sheath; tensioning the tether; and pointing the distal end of the inner catheter in a third direction; and moving the distal end of the wire guide through the distal end of the inner catheter in the third direction.

These and other advantages, effects, and features of the invention will become better understood from the description and claims that follow. In the description, reference is made to the accompanying drawings, which form a part hereof and in which there is shown by way of illustration, not limitation, embodiments of the invention.

BRIEF DESCRIPTION OF THE DRAWINGS

Like reference numerals will be used to refer to like parts from Figure to Figure in the following description of the drawings.

DETAILED DESCRIPTION

The guide catheter assemblies and methods now will be described more fully hereinafter with reference to the accompanying drawings, in which some, but not all embodiments of the invention are shown. Indeed, the invention may be embodied in many different forms and should not be construed as limited to the embodiments set forth herein.

Likewise, many modifications and other embodiments of the assemblies and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, certain example methods and materials are described herein.

Overview and Industrial Applicability

The present disclosure is generally applicable to guide catheter assemblies for use in percutaneous endovascular procedures. More specifically, the present disclosure finds application in procedures that require numerous direction changes while navigating the vascular system of an individual, which can be a mammal, preferably a human. Further, the present disclosure finds specific application in procedures during which it is desirable to reverse directions of a wire guide without establishing a new access site.

Guide Catheter Assemblies

Figure 1:
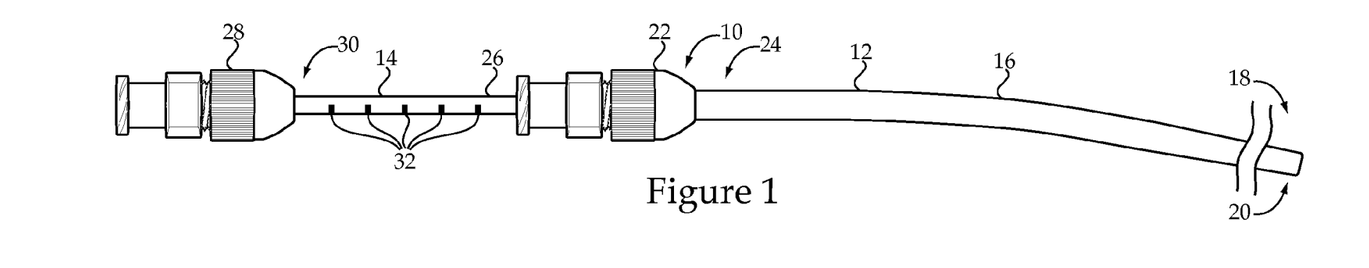
FIG. 1 is a side view of a guide catheter assembly according to the present disclosure.

Referring to FIG. 1, there is shown a guide catheter assembly 10, or directional guide catheter assembly, that may be used in a variety of percutaneous endovascular procedures. The guide catheter assembly 10 generally includes an outer sheath 12 and an inner catheter 14, which is disposed, at least partially, within the outer sheath 12. The outer sheath 12 may include a flexible tube 16, and may be provided in any desired length. A distal end 18 of the outer sheath 12 may include a tapered segment, shown generally at 20, forming an atraumatic tip. A threaded fitting 22, such as a well-known Tuohy Borst adapter or other fitting, may be provided at a proximal end 24 of the outer sheath 12.

The inner catheter 14 may also comprise a flexible tube, shown at 26, and may have a threaded fitting 28, similar to threaded fitting 22, provided at a proximal end 30 thereof. One or both of the flexible tubes 16 and 26 may have a composite construction that includes a hollow shaft defined by an inner tube. The inner tube may comprise a lubricious material such as polytetrafluoroethylene (PTFE), commonly known by the brand name Teflon®. A reinforcement, such as a metal braid or coil, may surround the inner tube in order to provide kink resistance and torqueability, while retaining flexibility of the overall tubes 16 and 26. An outer tube may be formed from a polyether block amide material marketed under the trade name PEBAX® or another equivalent material that may be applied via a shrink wrap process. Alternatively, the flexible tubes 16 and 26 may include multi-layer tubes comprised of various other materials, or may even include single polymeric tubes. It should be appreciated that the materials and overall construction of the tubes 16 and 26 may be selected to improve or enhance usability of the guide catheter assembly 10.

At least a segment of the inner catheter 14 may be slidable within the outer sheath 12, and, as such, the materials comprising both the inner catheter 14 and outer sheath 12 may be selected to facilitate such movement. Threaded fittings 22 and 28, according to embodiments utilizing such fittings, may function as handles to affect the sliding movement. For example, the threaded fittings 22 and 28 may be grasped to more easily move one of the inner catheter 14 and outer sheath 12 relative to the other. The inner catheter 14 may also include a plurality of direction indicators 32 along the proximal end 30 thereof, the use of which will be discussed below.

Figure 2:
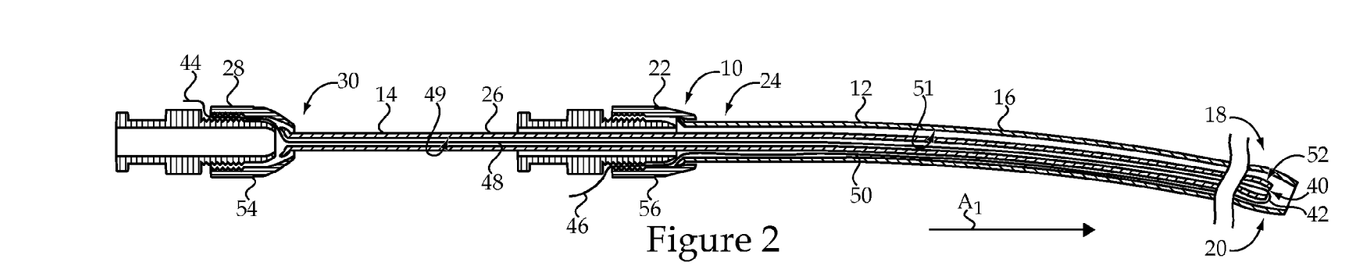
FIG. 2 is a cross-sectional view through the guide catheter assembly of FIG. 1 according to a first embodiment, shown in a first configuration.

Turning now to FIG. 2, a cross-sectional view of the guide catheter assembly 10 according to one exemplary embodiment is shown. In all embodiments, the guide catheter assembly 10 will include a tether 40 or other similar device connecting or, more specifically, tethering the inner catheter 14 to the outer sheath 12. According to the embodiment of FIG. 2, the tether 40 includes a flexible thread 42 having a first end 44 connected to the proximal end 30 of the inner catheter 14 and a second end 46 connected to the proximal end 24 of the outer sheath 12. A first segment 48 of the flexible thread 42 may be disposed within an inner cavity, or lumen, 49 of the inner catheter 14, while a second segment 50 of the flexible thread 42 may be disposed within a space, shown generally at 51, defined by an outer diameter of the inner catheter 14 and an inner diameter of the outer sheath 12.

As shown, the first end 44 of the flexible thread 42 may be connected to the inner catheter 14 by threaded fitting 28, while the second end 46 of the flexible thread 42 may be connected to the outer sheath 12 by threaded fitting 22. For example, each of the threaded fittings 22 and 28 may comprise two components that are joined by engaging external threads of one of the components with internal threads of the other component, such as by rotating one component relative to the other. Each of the ends 44 and 46 of the flexible thread 42 may be secured within the threads of the fittings 22 and 28, respectively, to connect the flexible thread 42 to the inner catheter 14 and outer sheath 12. Although specific attachment means are provided, it should be appreciated that any attachment means may be used to permanently or temporarily connect ends 44 and 46 of the flexible thread 42 to the inner sheath 14 and outer sheath 12, respectively.

Flexible thread 42 may comprise any fiber or combination of fibers, such as, for example, polyester, silk, or cotton. Although a wide variety of materials may be selected for flexible thread 42, thread 42 will not include a metallic material. It should be appreciated that the composition of flexible thread 42 may be selected to achieve a desired size or fineness, strength and elasticity, based on the use of flexible thread 42 within guide catheter assembly 10. Such use will be described below in greater detail.

The guide catheter assembly 10 is shown in a first configuration in FIG. 2. Specifically, according to the first configuration, the tether 40 or, more specifically, the flexible thread 42 of the current embodiment is untensioned and distal ends 18 and 52 of the outer sheath 12 and inner catheter 14, respectively, are pointing in a first direction, represented by arrow $A_1$. This configuration may also be referred to as a "relaxed" configuration, characterized in that the distal ends 18 and 52 are pointing in the same direction and the tether 40 is untensioned, and may be the preferred configuration for moving or advancing the guide catheter assembly 10 through a vascular structure of an individual.

Figure 3:
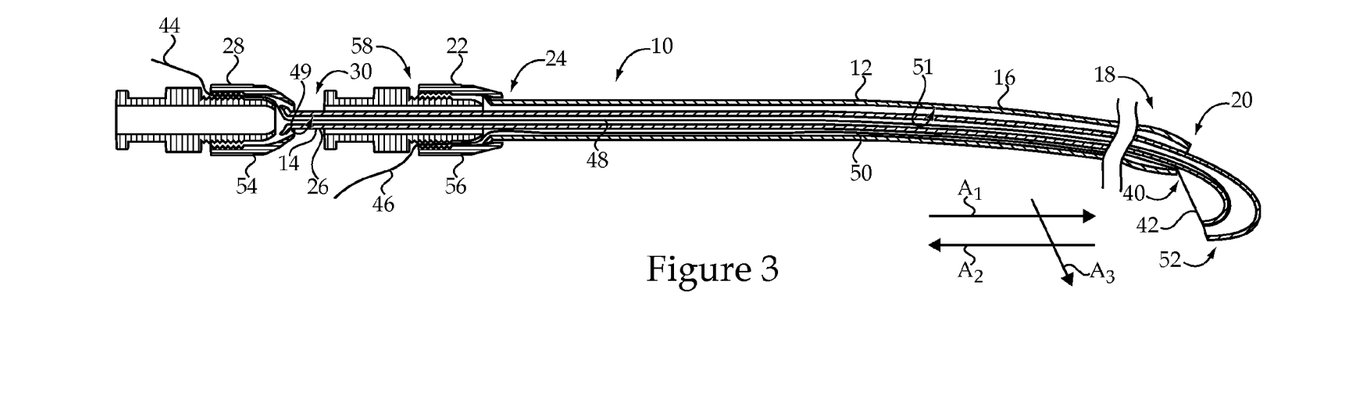
FIG. 3 is a cross-sectional view through the guide catheter assembly of FIG. 1 according to the first embodiment, shown in a second configuration.

Turning now to FIG. 3, a second configuration, or "curved" configuration, of the guide catheter assembly 10 according to the first embodiment is shown. According to the second configuration, the tether 40, or flexible thread 42, is tensioned, the distal end 18 of the outer sheath 12 is pointing in the first direction $A_1$ and the distal end 52 of the inner catheter 14, which may also include an atraumatic tip, is pointing in a second direction, represented by arrow $A_2$. As shown, the second direction $A_2$ may be opposite the first direction, for example, oriented at a 180° angle with respect to the first direction $A_1$. However, it should be appreciated that the guide catheter assembly 10 may be configured to point the distal end 52 of the inner catheter 14 in any of a continuous range of directions with respect to the distal end 18 of the outer sheath 12. As such, the curved configuration may be characterized in that the distal ends 18 and 52 are pointing in different directions and the tether 40 is tensioned. Further, the tether 40, in such a configuration, is oriented at an angle $A_3$ that is different from both directions $A_1$ and $A_2$.

As used herein, a "different" direction may include any direction that is oriented at an angle greater than 0° with respect to another direction. For example, direction $A_1$ may be considered different from direction $A_2$ if they are oriented at angles separated by at least 1°. As such, guide catheter assembly 10 can be manipulated to accommodate any curves, including slight curves and sharp curves. Although an "opposite" direction may represent a direction that is oriented at a 180° angle with respect to another direction, as described above, the opposite direction preferably represents an opposite direction with respect to blood flow. For example, a retrograde direction is opposite an antegrade direction with respect to blood flow.

It should be appreciated that the tether 40 is chosen to have a length that limits a range of movement of the distal end 52 of the inner catheter 14 relative to the distal end 18 of the outer sheath 12. Preferably, the guide catheter assembly 10 is configured so that the inner catheter 14 is greater in length than the outer sheath 12. As a result, when the distal end 52 of the inner catheter 14 is advanced through the distal end 18 of the outer sheath 12, such that the distal end 52 of the inner catheter 14 is no longer disposed within the outer sheath 12, the tether 40 will become tensioned and will cause the distal end 52 of the inner catheter 14 to curve, or point in a different direction.

It may be desirable to provide a side port through the distal end 52 of the inner catheter 14, and position the tether 40, or flexible thread 42, through the side port rather than through the distal end opening, as shown. It should be appreciated that, according to the current embodiment, continued use of the guide catheter assembly 10 may cause the tether 40 to pull or tear the distal end opening, thus compromising the atraumatic tip. As a solution, the tether 40, or flexible thread 42, may be positioned away from the atraumatic tip, as disclosed.

To facilitate the movement described above, threaded fitting 28 may function as a first handle 54, while threaded fitting 22 may function as a second handle 56. It should be appreciated, however, that handles 54 and 56, if provided, may be independent from fittings 28 and 22, depending on design preferences. Movement of the inner catheter 14 relative to the outer sheath 12 may be facilitated by moving one of the handles 54 and 56 relative to the other. As shown, the first handle 54 is closer to the second handle 56 in the second configuration, shown in FIG. 3, than in the first configuration, shown in FIG. 2.

Direction indicators 32, shown in FIG. 1, may be provided in any of the embodiments contemplated herein to assist in selecting a desired direction of the distal end 52 of the inner catheter 14 relative to the distal end 18 of the outer sheath 12 during use of the guide catheter assembly 10. Specifically, the inner catheter 14 may be moved relative to the outer sheath 12 so that one of the direction indicators 32 corresponding to a desired direction is substantially aligned with the proximal end 24, or threaded fitting 22, of the outer sheath 12. Any number of direction indicators 32 may be provided and may represent common direction changes in percutaneous endovascular procedures. For instance, each successive direction indictor 32 may represent an additional 45° turn in direction.

Once the guide catheter assembly 10 is moved to a desired configuration, whether it be the second configuration of FIG. 2 or any other curved configuration, it may be desirable to lock a position of the inner catheter 14 relative to the outer sheath 12. Specifically, a locking device 58 may be provided to lock the inner catheter 14 relative to the outer sheath 12 at any position, such as any of a continuum of positions between the first configuration and second configuration. As should be appreciated, the second direction $A_2$ may represent the 180° angle shown in FIG. 3 or any other angle, including a negative angle, a 360° angle, or an even greater angle, all with respect to direction $A_1$.

The locking device, represented generally at 58, may be an inherent feature of threaded fitting 22. For example, conventional Tuohy Borst adapters may include a screw mechanism that may be rotated to drive a component axially inward to compress an O-ring or similar device, which may restrict movement of the inner catheter 14 within the outer sheath 12. However, it should be appreciated that any well-known locking devices, which may or may not be integral with threaded fitting 22 may be used to maintain a selected configuration of the guide catheter assembly 10.

Figure 4:
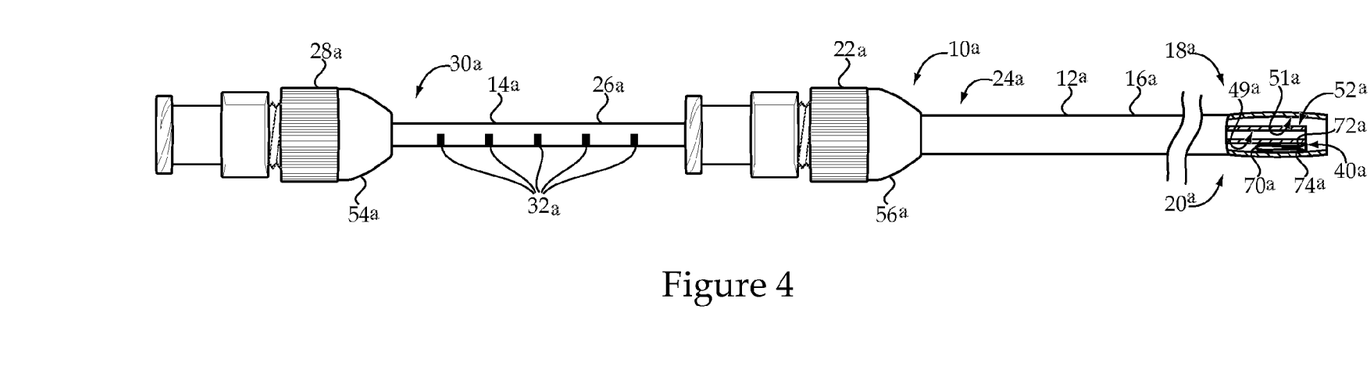
FIG. 4 is a side view, partially in cross-section, of a guide catheter assembly according to a second embodiment, shown in a first configuration.

Turning now to FIG. 4, a second exemplary embodiment of the guide catheter assembly 10a is shown. Specifically, a partially cross-sectioned view of the guide catheter assembly 10a is shown to illustrate an alternative tether 40a that may be used in guide catheter assembly 10a. According to the second embodiment, the tether 40a may include a wall segment 70a, which may be provided from one of the inner catheter 14a and outer sheath 12a. Specifically, a portion of the one or more layers of one of the inner catheter 14a and outer sheath 12a may be cut away from tubes 26a or 16a and used as the tether 40a. Alternatively, however, wall segment 70a may be constructed independently from the inner catheter 14a and outer sheath 12a. A first end 72a of the wall segment 70a may be connected to the distal end 52a of the inner catheter 14a, while a second end 74a of the wall segment 70a may be connected to the distal end 18a of the outer sheath 12a. It should be appreciated that the ends 72a and 74a may be connected to the inner catheter 14a and outer sheath 12a, respectively, at any location along the distal ends 52a and 18a deemed appropriate. However, they must be positioned close enough to distal ends to function as described herein.

Figure 5:
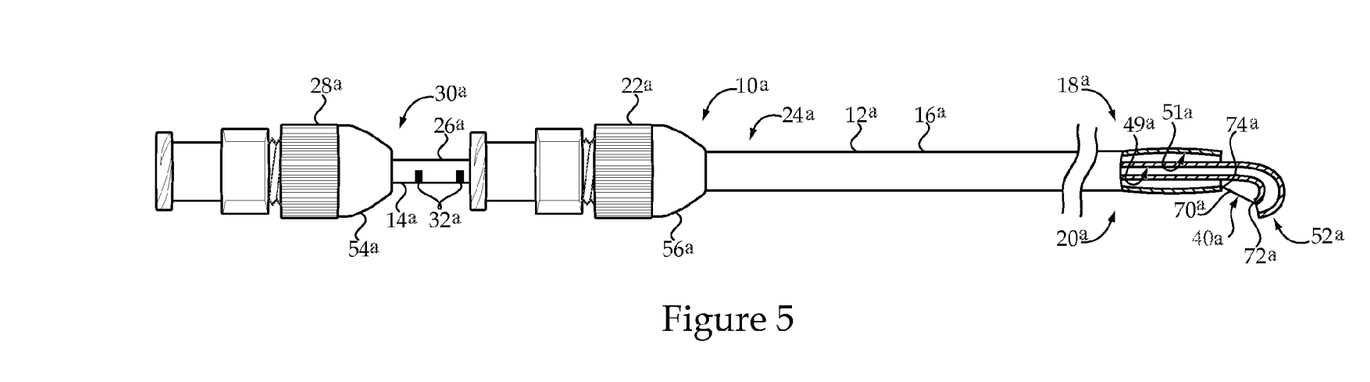
FIG. 5 is a side view, partially in cross-section, of the guide catheter assembly of FIG. 4, shown in a second configuration.

The second embodiment, including the wall segment 70a, is shown in the first or relaxed configuration, described above, in FIG. 4, and in the second or curved configuration, also described above, in FIG. 5. As described, in the first configuration, the tether 40a or, more specifically, the wall segment 70a of the current embodiment is untensioned and the distal ends 18a and 52a of the outer sheath 12a and inner catheter 14a, respectively, are pointing in the first direction A₁. In the second configuration, the tether 40a, or wall segment 70a, is tensioned, the distal end 18a of the outer sheath 12a is pointing in the first direction A₁, and the distal end 52a of the inner catheter 14a is pointing in the second direction A₂.

As should be appreciated, the tether 40a may comprise a variety of materials and may be connected to the inner catheter 14a and outer sheath 12a at a number of different locations using any number of attachment means to provide the direction changing capabilities described herein. Although numerous options are available, it should be appreciated that the size of the flexible tubes 16a and the length and positioning of tether 40a may be selected to ensure the guide catheter assembly 10a, particularly when in the curved configuration, may safely be reconfigured within the vascular structures being treated. In addition, the attachment means may be highly dependent upon the specific tether 40a being used. For instance, opposite ends of the tether 40a, such as ends 72a and 74a of wall segment 70a, may be melt bonded to the inner catheter 14a and outer sheath 12a if the materials selected are the same.

The distal end 18a of the outer sheath 12a may include a tapered segment, shown generally at 20a, forming an atraumatic tip. A threaded fitting 22a, such as a well-known Tuohy Borst adapter or other fitting, may be provided at a proximal end 24a of the outer sheath 12a. The inner catheter 14a may have a threaded fitting 28a, similar to threaded fitting 22a, provided at a proximal end 30a thereof. To facilitate the movement described above, threaded fitting 28a may function as a first handle 54a, while threaded fitting 22a may function as a second handle 56a. Direction indicators 32a, shown in FIG. 4, may be provided to assist in selecting a desired direction of the distal end 52a of the inner catheter 14a relative to the distal end 18a of the outer sheath 12a during use of the guide catheter assembly 10a.

Methods

Figure 6:
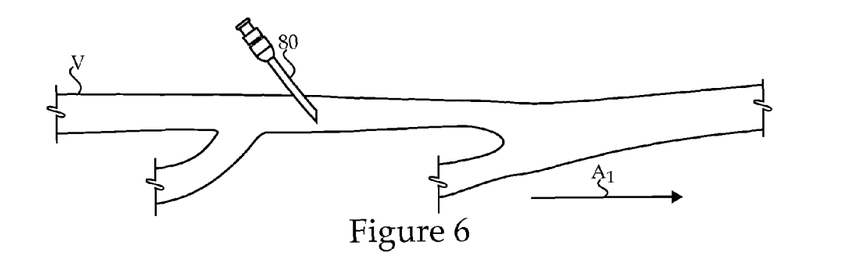
FIG. 6 is a side diagrammatic view of a vascular structure of an individual at one stage of a percutaneous endovascular procedure, according to one aspect of the present disclosure.
Figure 7:
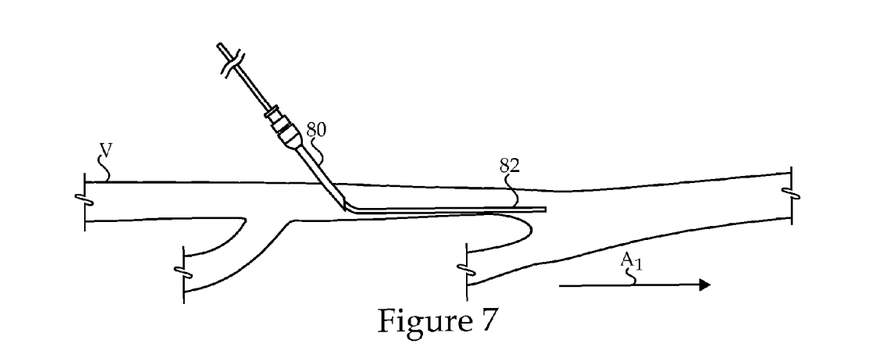
FIG. 7 is a side diagrammatic view of the vascular structure of an individual at another stage of a percutaneous endovascular procedure, according to one aspect of the present disclosure.
Figure 8:
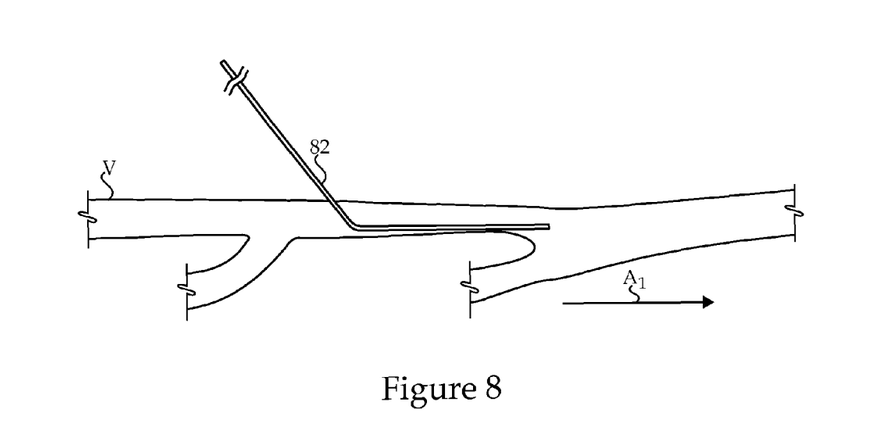
FIG. 8 is a side diagrammatic view of the vascular structure of an individual at yet another stage of a percutaneous endovascular procedure, according to one aspect of the present disclosure.

Referring to FIG. 6, there is shown a vascular structure V of an individual having a needle, or introducer, 80 positioned therein, at a first stage of an endovascular procedure according to one embodiment. The procedure, further described herein, may include a percutaneous endovascular procedure such as an angioplasty procedure, a stent placement or retrieval procedure, a vascular filter placement or retrieval procedure, an imaging procedure, or any other known procedure. At a next stage of the procedure, shown in FIG. 7, a clinician may insert a wire guide 82 through a tube of the needle 80 and into the vascular structure V. Based on the orientation of the needle 80, the wire guide 82 may be inserted in a retrograde direction with respect to a blood flow direction in vascular structure V. According to the exemplary procedure, the retrograde direction may correspond substantially with the first direction, represented by arrow A₁. After the wire guide 82 is inserted into the vascular structure V, the needle 80 may be removed, as shown in FIG. 8. As should be appreciated, the wire guide 82 now serves as a means of access to the vascular structure V.

Figure 9:
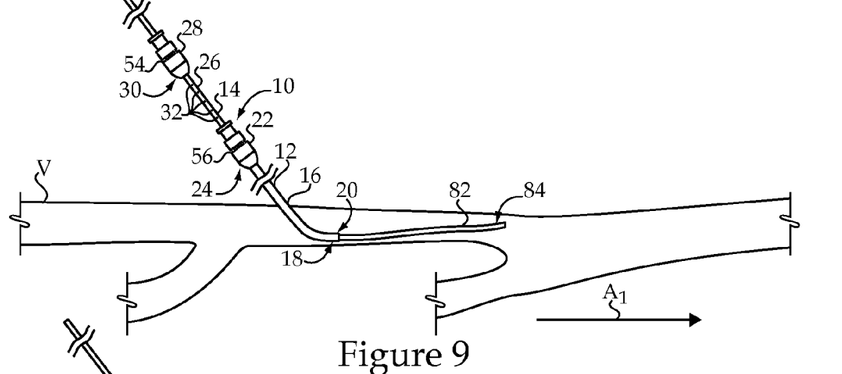
FIG. 9 is a side diagrammatic view of the vascular structure of an individual at yet another stage of a percutaneous endovascular procedure, according to one aspect of the present disclosure.

Turning now to FIG. 9, the guide catheter assembly 10, which may preferably be in a relaxed configuration, may be inserted over the wire guide 82 and advanced to a desired location within the vascular structure V. For example, the guide catheter assembly 10, with the assistance of ultrasound or radiography, may be inserted such that the distal end 18 of the outer sheath 12 is at a location in the vascular structure V where a position change is desired. Alternatively, the guide catheter assembly 10 may be inserted to reverse the direction of the wire guide 82 within the vascular structure V. Once positioned, and if necessary, the wire guide 82 will be retracted such that a distal end 84 is received entirely within the guide catheter assembly 10. At this stage of the procedure, shown generally in FIG. 10, the guide catheter assembly 10 may be configured to redirect the wire guide 82 in a new direction. For example, it may be desirable to convert a retrograde puncture, shown in FIG. 6, to an antegrade catheterization.

The guide catheter assembly 10 may be moved from the first or relaxed configuration, shown in FIG. 2, to the second or curved configuration, shown in FIG. 3. Likewise, the guide catheter assembly 10a may be moved from the first or relaxed configuration, shown in FIG. 4, to the second or curved configuration, shown in FIG. 5. Although the guide catheter assembly 10 of FIGS. 2 and 3 uses flexible thread 42 as the tether 40 and guide catheter assembly 10a of FIGS. 4 and 5 use wall segment 70a as the tether 40a, it should be appreciated that any similar structure or feature providing the same tethering action as described herein may be used. Further, although two specific configurations, namely the first configuration and the second configuration, have been shown, it should be appreciated that the guide catheter assembly 10 and the guide catheter assembly 10a may be moved to a number of different configurations, each configuration pointing the distal end of the inner catheter in a different direction.

Figure 10:
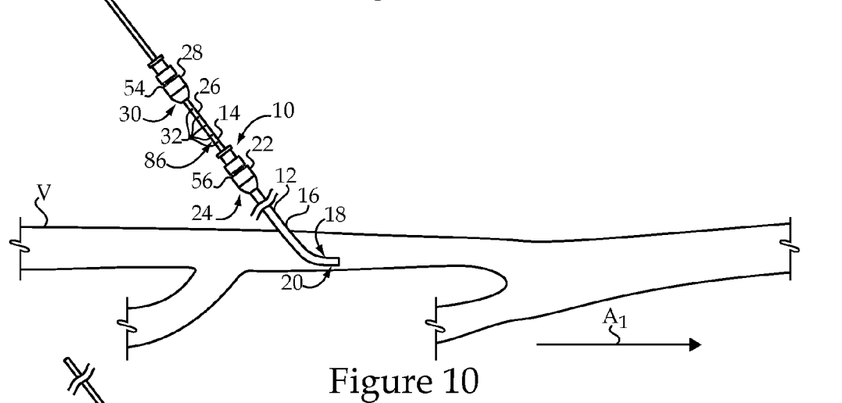
FIG. 10 is a side diagrammatic view of the vascular structure of an individual at yet another stage of a percutaneous endovascular procedure, according to one aspect of the present disclosure.

More specifically, in the first configuration, shown generally in FIG. 10, the distal end 52 of the inner catheter 14 and the distal end 18 of the outer sheath 12 are pointing in the first direction, corresponding substantially to direction A₁. The guide catheter assembly 10 may be moved from the first configuration of FIG. 10 by sliding a segment 86 of the inner catheter 14 within the outer sheath 12, such as by moving the threaded fitting 28, or first handle 54, closer to the threaded fitting 22, or second handle 56. Such movement causes the distal end 52 of the inner catheter 14 to move in the first direction, represented by arrow A₁, until the distal end 52 is restrained, or tethered, by the tether 40.

Figure 11:
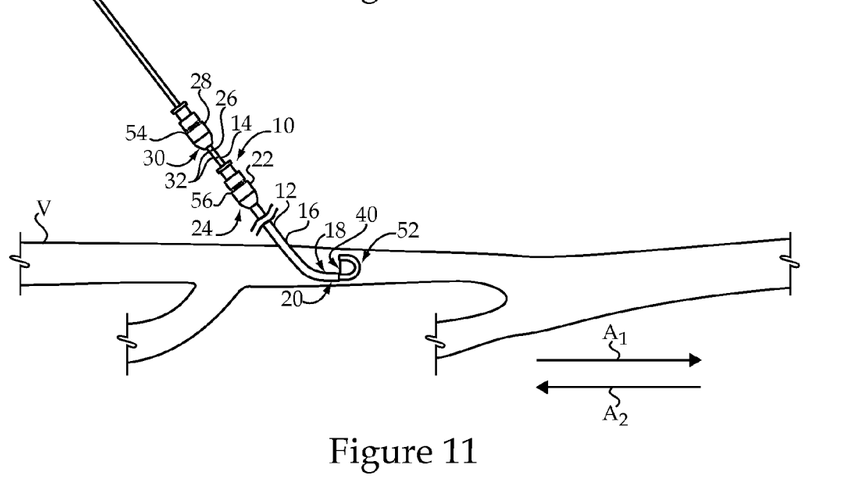
FIG. 11 is a side diagrammatic view of the vascular structure of an individual at yet another stage of a percutaneous endovascular procedure, according to one aspect of the present disclosure.

When the tether is tensioned, as shown in FIG. 11, continued movement of the proximal end 30 of the inner catheter 14 causes the tether 40 to point the distal end 52 of the inner catheter 14 in the second direction, represented by arrow A₂. According to the exemplary procedure, the second direction A₂ is opposite the first direction A₁, which may correspond to one of direction indicators 32. However, the guide catheter assembly 10 may be moved to redirect the wire guide 82 to any direction required by the procedure. If desired, a locking device 58 may anchor the inner catheter 14 relative to the outer sheath 12 to maintain the second configuration of the guide catheter assembly 10.

Figure 12:
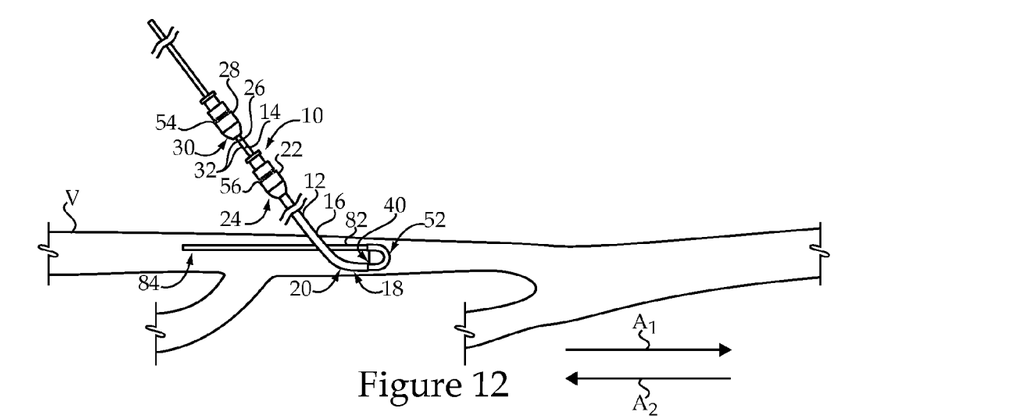
FIG. 12 is a side diagrammatic view of the vascular structure of an individual at yet another stage of a percutaneous endovascular procedure, according to one aspect of the present disclosure.

At a next stage of the procedure, shown in FIG. 12, the distal end 84 of the wire guide 82 may be moved through the distal end 52 of the inner catheter 14 in the second direction A₂. According to the exemplary procedure, the second direction, represented by arrow A₂, may represent an antegrade direction with respect to the blood flow direction.

Figure 13:
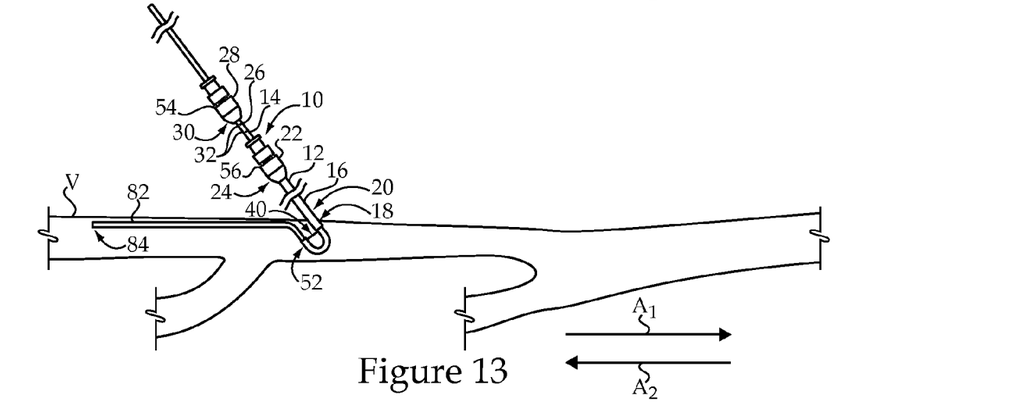
FIG. 13 is a side diagrammatic view of the vascular structure of an individual at yet another stage of a percutaneous endovascular procedure, according to one aspect of the present disclosure.
Figure 14:
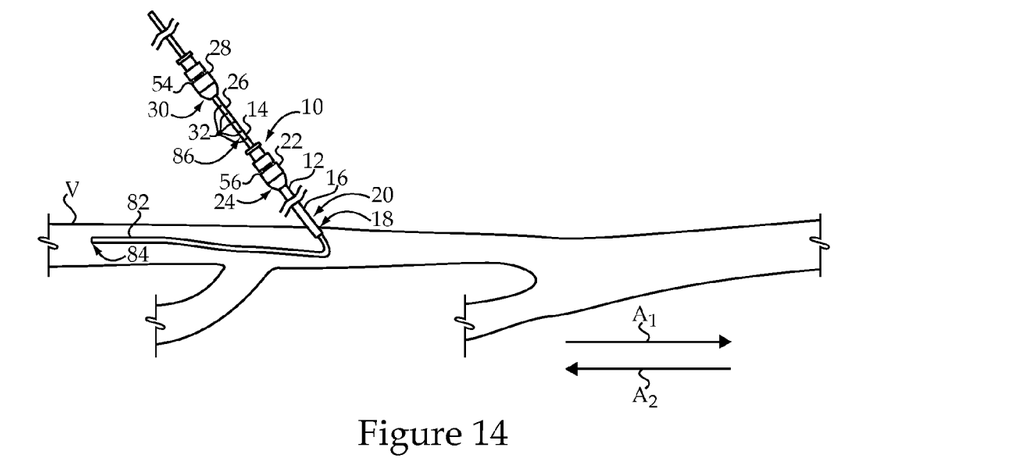
FIG. 14 is a side diagrammatic view of the vascular structure of an individual at yet another stage of a percutaneous endovascular procedure, according to one aspect of the present disclosure.
Figure 15:
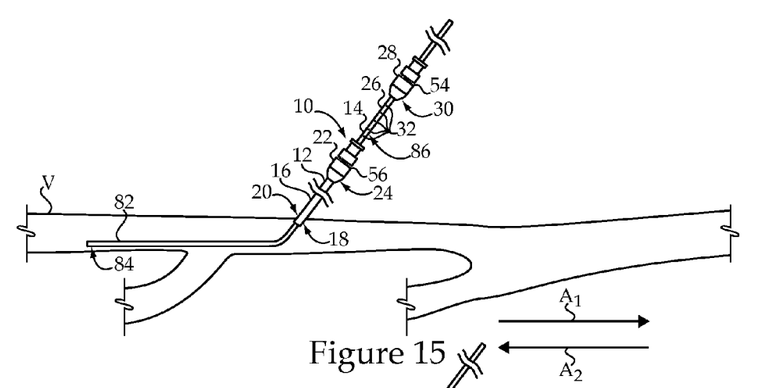
FIG. 15 is a side diagrammatic view of the vascular structure of an individual at yet another stage of a percutaneous endovascular procedure, according to one aspect of the present disclosure.

Turning now to FIG. 13, the guide catheter assembly 10 may be pulled back toward the access site until the clinician feels a resistance. At that point, as shown in FIG. 14, the guide catheter assembly 10 may be relaxed, at least in part, by sliding the segment 86 of the inner catheter 14 out of the outer sheath 12 and untensioning the tether 40. The guide catheter assembly 10 may then be reoriented, as shown in FIG. 15, such that the distal end 52 of the inner catheter 14 and distal end 18 of the outer sheath 12 are pointing substantially in the second direction $A_2$.

Figure 16:
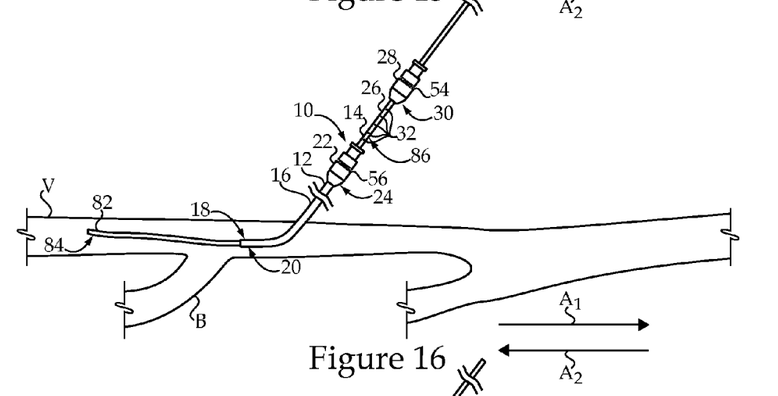
FIG. 16 is a side diagrammatic view of the vascular structure of an individual at yet another stage of a percutaneous endovascular procedure, according to one aspect of the present disclosure.

During the same procedure, it may be desirable to accommodate numerous direction changes. For example, after the guide catheter assembly 10 has been used to redirect the wire guide 82 from the first or retrograde direction $A_1$ to the second or antegrade direction $A_2$, it may be desirable to redirect the wire guide 82 again to maneuver into another vascular structure or branch, such as branch B. To redirect the wire guide 82 again, the guide catheter assembly 10 must be moved further within the vascular structure 10 in the second direction $A_2$ such that the distal end 18 of the outer sheath 12 is substantially aligned with branch B, as shown in FIG. 16.

Figure 17:
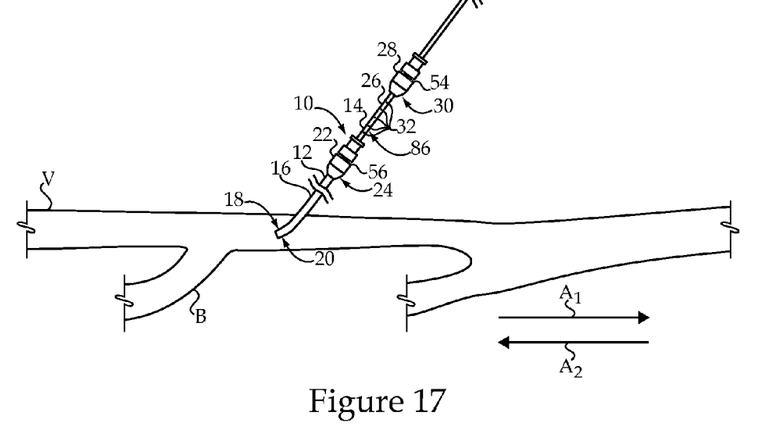
FIG. 17 is a side diagrammatic view of the vascular structure of an individual at yet another stage of a percutaneous endovascular procedure, according to one aspect of the present disclosure.
Figure 18:
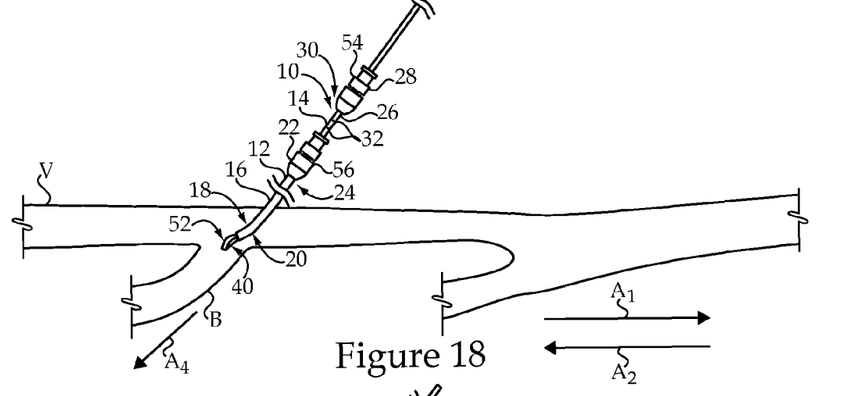
FIG. 18 is a side diagrammatic view of the vascular structure of an individual at yet another stage of a percutaneous endovascular procedure, according to one aspect of the present disclosure.

Once positioned, and if necessary, the wire guide 82 may be retracted such that the distal end 84 is received entirely within the guide catheter assembly 10. At this stage of the procedure, shown generally in FIG. 17, the guide catheter assembly 10 may be configured to redirect the wire guide 82 in a new direction. Specifically, the guide catheter assembly 10 may be moved from a third configuration, in which the tether 40 is untensioned and the distal ends 52 and 18 of the inner catheter 14 and outer sheath 12 are pointing in the second direction $A_2$, to a fourth configuration, shown in FIG. 18. In the fourth configuration, the tether 40 is tensioned, the distal end 18 of the outer sheath 12 is pointing in the second direction $A_2$, and the distal end 52 of the inner catheter 14 is pointing in a third direction, represented by arrow $A_4$. It should be appreciated that the third configuration may also be referred to as a relaxed configuration, while the fourth configuration may be referred to as a curved configuration, both of which are described above.

Figure 19:
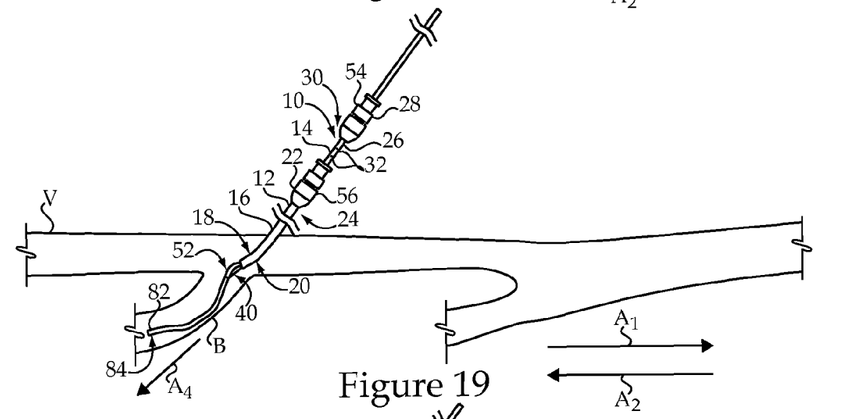
FIG. 19 is a side diagrammatic view of the vascular structure of an individual at yet another stage of a percutaneous endovascular procedure, according to one aspect of the present disclosure.
Figure 20:
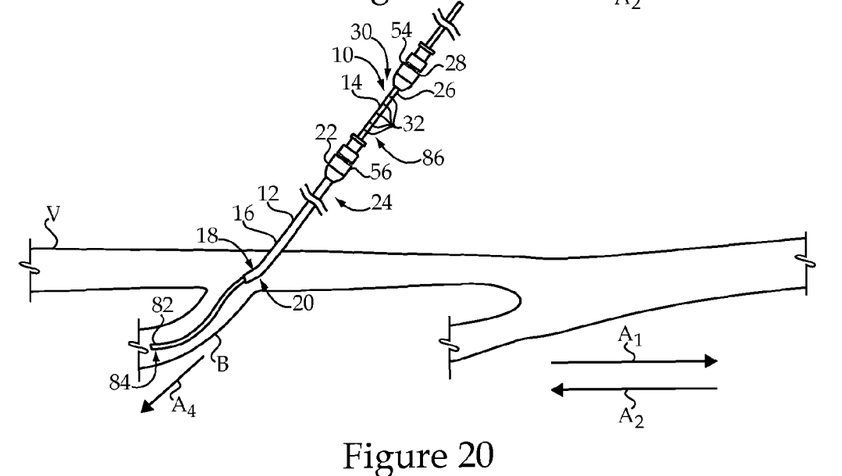
FIG. 20 is a side diagrammatic view of the vascular structure of an individual at yet another stage of a percutaneous endovascular procedure, according to one aspect of the present disclosure.

Turning now to FIG. 19, the distal end 84 of the wire guide 82 may be moved through the distal end 52 of the inner catheter 14 in the third direction $A_4$. As shown, the wire guide 82 is now located in branch B. After the wire guide 82 is successfully positioned at the desired location, such as that shown in FIG. 20, the clinician may pull the guide catheter assembly 10 back toward the access site until the clinician feels resistance, and may remove the curve by relaxing the guide catheter assembly 10, at least in part, by sliding segment 86 of the inner catheter 14 out of the outer sheath 12 and untensioning the tether 40. If no additional direction changes are needed, the clinician may remove the guide catheter assembly 10 from the individual.

In addition, according to one specific procedure, the guide catheter assembly 10 may be used in the treatment of stenosis in arteries of both legs. For example, a clinician may establish a retrograde puncture in one leg of an individual, such as in an obese individual, where an antegrade puncture may be difficult. The clinician may then utilize the guide catheter assembly 10 to lead the wire guide 82 to the opposite leg of the individual, utilizing the guide catheter assembly 10 as described above. After the opposite leg of the individual is treated, the clinician may use the guide catheter assembly 10 to reverse the retrograde direction of the wire guide 82 in the first leg to the antegrade direction and treat that leg of the individual. As a result, both legs of the individual may be treated without the need to establish an additional access site.

As should be appreciated, the guide catheter assembly 10 described herein may be useful in any percutaneous endovascular procedures in which one or more direction changes are needed. Specifically, the distal end 52 of the inner catheter 14 may be dynamically redirected during a procedure to accommodate any desired direction change, including a direction reversal. Such dynamic redirection reduces the need for removal and insertion of wire guides and/or guide catheters having specific preformed curves and reduces the need to establish new access sites to achieve direction reversals. Further, the guide catheter assembly 10 described herein includes a cost effective design that requires minimal additional parts occupying a minimal amount of space of the guide catheter assembly 10.

The present invention has been described in connection with certain embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims

What is claimed is:

1. A guide catheter assembly, comprising:
   an outer sheath having a distal end, a proximal end, and an inner diameter;
   an inner catheter disposed, at least partially, within the outer sheath, the inner catheter having a distal end, a proximal end, and an outer diameter; and
   a tether tethering the inner catheter to the outer sheath, the tether including (i) a first end directly connected to the proximal end of the inner catheter, (ii) a first segment disposed within the inner catheter, (iii) a second segment disposed within a space defined by the inner diameter of the outer sheath and the outer diameter of the inner catheter, and (iv) a second end directly connected to the proximal end of the outer sheath;
   the guide catheter assembly having a first configuration wherein the tether is untensioned, the distal end of the outer sheath is pointing in a first direction, and the distal end of the inner catheter is pointing in the first direction, and a second configuration wherein the tether is tensioned, the distal end of the outer sheath is pointing in the first direction, the distal end of the inner catheter is pointing in a second direction that is different from the first direction, and the tether is oriented at an angle different from both the first direction and the second direction.

2. The guide catheter assembly of claim 1, wherein the inner catheter is greater in length than the outer sheath.

3. The guide catheter assembly of claim 2, wherein the second direction is opposite the first direction.

4. The guide catheter assembly of claim 2, further including a first handle disposed along the proximal end of the inner catheter and a second handle disposed along the proximal end of the outer sheath, wherein the first handle is closer to the second handle in the second configuration than in the first configuration.

5. The guide catheter assembly of claim 2, further including a plurality of direction indicators positioned along the proximal end of the inner catheter, wherein one of the plurality of direction indicators corresponds to the second configuration.

6. The guide catheter assembly of claim 2, further including a locking device for fixing the inner catheter relative to the outer sheath at one of a continuum of positions between the first configuration and the second configuration.

7. The guide catheter assembly of claim 2, wherein the tether includes a flexible thread.

8. The guide catheter assembly of claim 7, further including a first threaded fitting connected to the proximal end of the inner catheter and a second threaded fitting connected to the proximal end of the outer sheath, wherein the first end of the flexible thread is connected to the inner catheter by the first threaded fitting and the second end of the flexible thread is connected to the outer sheath by the second threaded fitting.

9. A method of positioning a guide catheter assembly, wherein the guide catheter assembly includes (a) an outer sheath having a distal end, a proximal end, and an inner diameter, (b) an inner catheter disposed, at least partially, within the outer sheath, the inner catheter having a distal end, a proximal end, and an outer diameter, and (c) a tether tethering the inner catheter to the outer sheath, the tether including (i) a first end directly connected to the proximal end of the inner catheter, (ii) a first segment disposed within the inner catheter, (iii) a second segment disposed within a space defined by the inner diameter of the outer sheath and the outer diameter of the inner catheter, and (iv) a second end directly connected to the proximal end of the outer sheath, the method comprising:
  moving the guide catheter assembly from a first configuration to a second configuration, wherein the moving step includes:
    pointing the distal end of the inner catheter and the distal end of the outer sheath in a first direction;
    sliding at least a segment of the inner catheter within the outer sheath;
    tensioning the tether; and
    pointing the distal end of the inner catheter in a second direction that is different from the first direction.

10. The method of claim 9, wherein the tensioning step includes limiting a range of movement of the distal end of the inner catheter relative to the distal end of the outer sheath using the tether.

11. The method of claim 10, further including locking the inner catheter relative to the outer sheath at one of a continuum of positions between the first configuration and the second configuration.

12. A method of performing a percutaneous endovascular procedure on an individual using a guide catheter assembly, wherein the guide catheter assembly includes (a) an outer sheath having a distal end, a proximal end, and an inner diameter, (b) an inner catheter disposed, at least partially, within the outer sheath, the inner catheter having a distal end, a proximal end, and an outer diameter, and (c) a tether tethering the inner catheter to the outer sheath, the tether including (i) a first end directly connected to the proximal end of the inner catheter, (ii) a first segment disposed within the inner catheter, (iii) a second segment disposed within a space defined by the inner diameter of the outer sheath and the outer diameter of the inner catheter, and (iv) a second end directly connected to the proximal end of the outer sheath, the method comprising: inserting a wire guide into a vessel of the individual in a first direction; inserting the guide catheter assembly over the wire guide; moving the guide catheter assembly from a first configuration to a second configuration, wherein the moving of the guide catheter assembly includes: pointing the distal end of the inner catheter and the distal end of the outer sheath in the first direction; sliding at least a segment of the inner catheter within the outer sheath; tensioning the tether; and pointing the distal end of the inner catheter in a second direction; and moving a distal end of the wire guide through the distal end of the inner catheter in the second direction.

13. The method of claim 12, wherein the tensioning step includes limiting a range of movement of the distal end of the inner catheter relative to the distal end of the outer sheath using the tether.

14. The method of claim 13, further including retracting the wire guide such that the distal end of the wire guide is received entirely within the guide catheter assembly prior to the moving of the guide catheter assembly.

15. The method of claim 14, wherein the sliding step includes moving the proximal end of the outer sheath to a direction indicator of the proximal end of the inner catheter.

16. The method of claim 14, wherein the moving of the guide catheter assembly further includes locking the inner catheter relative to the outer sheath to maintain the second configuration.

17. The method of claim 14, wherein the inserting of the wire guide includes inserting the wire guide in a retrograde direction with respect to a blood flow direction and the moving of the distal end of the wire guide includes moving the distal end of the wire guide in an antegrade direction with respect to the blood flow direction.

18. The method of claim 14, further including: moving the guide catheter assembly from a third configuration in which the tether is untensioned and the distal ends of the inner catheter and outer sheath are pointing in the second direction; to a fourth configuration in which the tether is tensioned, the distal end of the outer sheath is pointing in the second direction and the distal end of the inner catheter is pointing in a third direction.

* * * * *